United States Patent [19]

Kruse

[11] 4,454,337

[45] Jun. 12, 1984

[54] SEMICARBAZIDE INTERMEDIATES FOR PREPARING 4-SUBSTITUTED INDOLES

[75] Inventor: Lawrence I. Kruse, Philadelphia, Pa.

[73] Assignee: SmithKline Beckman Corporation, Philadelphia, Pa.

[21] Appl. No.: 471,572

[22] Filed: Mar. 2, 1983

Related U.S. Application Data

[60] Division of Ser. No. 278,016, Jun. 29, 1981, Pat. No. 4,394,514, which is a continuation-in-part of Ser. No. 259,123, Apr. 30, 1981, abandoned.

[51] Int. Cl.$^3$ .................... C07C 79/46; C07C 79/35; C07C 79/00
[52] U.S. Cl. .................................... 560/22; 568/424; 564/36
[58] Field of Search .................. 564/36; 568/424; 560/22

[56] References Cited

U.S. PATENT DOCUMENTS 3,753,680  8/1973  Tilles ................................. 564/36 X
4,063,025  12/1977  Murakami et al. ................... 560/29
4,214,001  7/1980  Engelhardt et al. ................ 424/300

FOREIGN PATENT DOCUMENTS 0004835  10/1979  European Pat. Off.
2153801  5/1972  Fed. Rep. of Germany.

Primary Examiner—Bernard Helfin
Attorney, Agent, or Firm—William H. Edgerton; Richard D. Foggio; Alan D. Lourie

[57] ABSTRACT

A new chemical sequence for preparing certain indoles is disclosed which employes certain 2-substituted-6-nitrophenylacetaldehyde semicarbazones claimed here. Said semicarbazones are cyclized to the indoles by low pressure hydrogenation.

4 Claims, No Drawings

SEMICARBAZIDE INTERMEDIATES FOR PREPARING 4-SUBSTITUTED INDOLES

This application is a divisional of application Ser. No. 278,016, filed June 29, 1981 and now U.S. Pat. No. 4,394,514, which is, in turn, a continuation-in-part of application Ser. No. 259,123 filed Apr. 30, 1981 and now abandoned.

This invention comprises both improvements in chemical processes for preparing indoles and certain new semicarbazone intermediates useful therein.

DESCRIPTION OF THE PRIOR ART

Low yields of certain substituted indoles were reported to have been found using a complex series of reactions involving a Reissert condensation including decarboxylation as the final step of the reaction sequence, K. G. Blaikie et al., J. Chem. Soc., 1924 296. In 1961, H. Meerwein et al., Am. Chem. 1961 641, described the condensation of the activated methyl groups of nitrotoluenes with amide acetals. A. D. Batcho et al., U.S. Pat. No. 3,976,639 described the preparation of indoles by a process which included the condensation of a o-nitrotoluene with a formamide acetal to give a $\beta$-dialkylamino-o-nitrostyrene which was then cyclized under standard reduction conditions. The object of the present invention is an improvement of the Batcho process.

DESCRIPTION OF THE INVENTION

I have found that, especially when certain bulky or deactivating groups are substituted on the o-nitrotoluene for example in the remaining ortho position, the reaction of o-nitrotoluene with a formamide acetal such as dimethylformamide dimethylacetal reacts sluggishly, often forming a substantial amount of polymeric side products. Substitution of tris-(dimethylamino)methane gives a more rapid homologation under mild conditions. Its use, as noted above, is particularly notable when there is a deactivating substituent ortho to the methyl group of the nitrotoluene starting material in the sequence which leads to the formation of 4-substituted indoles.

Substituents on the phenyl ring which are either chemically inert or usefully controlled under the conditions described herein are lower alkoxy, lower alkyl, benzyloxy, nitro, halo or carboalkoxy said alkoxy or alkyl groups being of 1–6 carbons preferably 1–2 carbons. Deactivating substituents are bulky alkoxy, carboalkoxy or alkyl groups.

The initial improvement of this invention is carried out by reacting the chosen o-nitrotoluene starting material with a slight excess of tris(dimethylamino)methane in an organic solvent in which the reactants are substantially soluble and which boils minimally within the temperature range of the reaction, such as about 100°–130° C., until the reaction is complete, usually about 1–6 hours. Variations of the temperature, solvent and time of reaction are possible by monitoring the progress of the reaction during the run using various chromatographic techniques known to the art. The product which is a $\beta$-dialkyl amino-o-nitrostyrene as described by Batcho is then either isolated by standard means or reacted in situ. Suitable organic solvents are dimethylsulfoxide, dimethylacetamide or dimethylformamide.

The $\beta$-dimethylamino-o-nitrostyrene is then cyclized by a reduction reaction as described in the cited prior art reference. Either catalytic hydrogenation such as using a noble metal catalyst for example 10% palladium on charcoal in ethanol or chemical reduction such as using ferrous sulfate in dilute ammonia gives the desired indole.

Unexpectedly as noted above certain substituents such as bulky or inactivating substituents especially at the o or 6-position of the styrene intermediate cause the formation of a large proportion of polymeric byproduct especially during ring closure. One may postulate this to be due to ready solubility of the styrenes. This problem has now been solved by converting the desired $\beta$-dimethylamino-o-nitrostyrene to a semicarbazone prior to reduction such as by reacting the $\beta$-dimethylamino styrene with a slight excess of semicarbazide, conveniently as an acid addition salt, either in situ or as a fresh reaction. Usually the reaction mixture comprises the reactants in aqueous dimethylacetamide or dimethylformamide. Ambient temperature is often used. Reaction is very quick usually up to one hour completes reaction. The semicarbazone is then either isolated by standard means or used in situ.

The ring closure of the semicarbazone synthon is carried out under reaction conditions similar to those disclosed for cyclizing as mentioned in U.S. Pat. No. 3,976,639. For example, any means of reduction may be used such as catalytic hydrogenation using a noble metal catalyst such as a palladium catalyst or Raney nickel at moderate pressures of hydrogen in a solvent in which the semicarbazide is soluble such as a lower alcohol. Alternatively a conventional chemical reduction reaction may be used such as ferrous sulfate in dilute ammonia, stannous chloride/hydrochloric acid, sodium dithionite, an alkali metal sulfide or hydrosulfide, iron-acid and the like usually at ambient or slightly elevated temperatures. Reduction of the ring substituents may take place at the same time such as when a nitro or benzyloxy group is present.

The desired indole is isolated in high yield and good purity by standard chemical methods.

Exemplary of the scope of the processes and intermediates of this invention are the following:

Scheme A

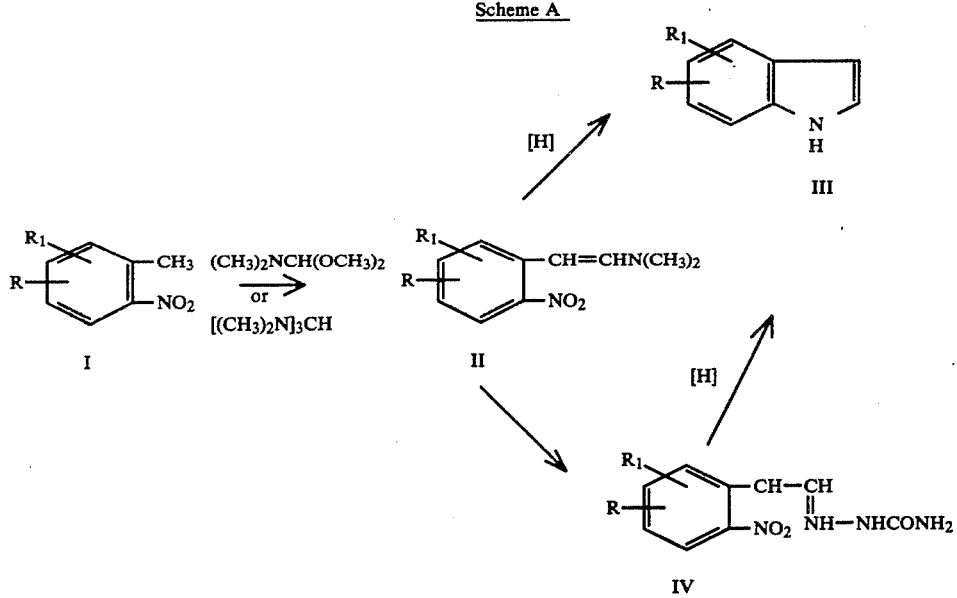

Wherein R and $R_1$ are each hydrogen, lower alkyl, nitro, cyano, lower alkoxy, benzyloxy, halo, that is fluoro, bromo, chloro or iodo, carboalkoxy or, when taken together on adjacent positions, methylenedioxy or ethylenedioxy, said alkyl, lower alkoxy or carboalkoxy groups having from 1-6 carbons in the alkoxy or alkyl groups, preferably 1-2 carbons. In the intermediate semicarbazide of Formula II R or $R_1$ may be nitro or any other substituent which will not be effected uncontrollably during the reaction. The methods and semicarbazone derivatives of this invention as noted above are particularly useful when the β-amino-o-nitrostyrene is either sluggish to form of difficult to cyclize because of side reactions. For example, most useful are the improvements of this invention applied to the reaction Scheme A in which $R_1$ is hydrogen and R is in the position ortho to the methyl substituent of the nitrotoluene (I) especially $R_1$ should be lower alkoxy, lower alkyl, benzyloxy or carboalkoxy. Most notable are the 4-alkoxyindoles which are difficult to prepare by prior art methods.

Ingredients of this invention therefore are the improvement of the reaction, I→II→III, in which tris(dimethylamino)methane is used in the reaction, I→II; certain of the semicarbazones (IV); and the reaction II→IV→III.

The end product indoles of this invention are general synthons and have utility as fine chemicals. The 4-substituted indoles which are particular target compounds of this invention are useful intermediates for preparing ergoline-like amines, pindolol, psilocin or dehydrobufotenine.

The following examples are intended to teach the practice of this invention. Temperatures are in Centigrade degrees.

EXAMPLE 1

A 1 liter flask equipped with reflux condenser and magnetic stirrer was flushed with argon and charged with 50% sodium hydride dispersion (9.6 g, 0.2 m). The dispersion was washed with two 100 ml portions of hexane, then suspended in dry dimethylformamide (100 ml) during the slow (foaming!) addition of 2-methyl-3-nitrophenol (30.62 g, 0.2 m). The red solution was cooled, and iodomethane (18.6 ml, 0.3 mole) was added rapidly. The solution was heated at 90° in an oil bath for 20 minutes. Tris(dimethylamino)methane (43.5 g, 0.3 m) was added followed by further heating at 115° for 3 hours. The mixture was cooled and a solution of semicarbazide hydrochloride (23.4 g, 0.21 m) and concentrated hydrochloric acid (18 ml, 0.22 m) in water (250 ml) was added. The tan mixture was cooled and filtered. The recovered precipitate was washed sequentially with water (500 ml), ice-cold ethanol (150 ml), and ether (250 ml), then dried to give 41.08 g (81.5%) of 2-methoxy-6-nitrophenylacetaldehyde semicarbazone as tan crystals, mp 205°-7° (d); mass spec. m/e 252 (M+).

A suspension of the semicarbazone (18 g, 0.071 m) in ethanol (150 ml) was hydrogenated over 10% palladium on carbon (4 g) for 6 hours at 60 psi, then filtered and concentrated. The residue was triturated with water (100 ml), filtered and dried. The crude crystalline indole was purified in a sublimation apparatus equipped with a dry-ice cold trap (85°/0.3 mm). The resulting sublimate was recrystallized from boiling chloroform (30 ml) by the addition of hot hexane (150 ml) giving 8.6 g (82%) of 4-methoxyindole as pure white crystals, mp 68°-70° (lit. 69°).

Repeating the above reaction but substituting 0.3 moles of butyl iodide gives 2-butoxy-6-nitrophenylacetaldehyde semicarbazone and 4-butoxyindole.

EXAMPLE 2

A mixture of 4.53 g (0.03 m) of o-nitroxylene, 5.22 g (0.036 m) of tris(dimethylamino)methane and 16 ml of dimethylformamide was heated at 115° (reflux) for 24 hours. A solution of 11.1 (0.1 m) of semicarbazide hydrochloride in 20 ml of water was added. Cooling and water washing gave 6.23 g (88%) of brown crystals of 2-methyl-6-nitrophenylacetaldehyde semicarbazone, mp 216°-217° (dec), mass spec. m/e 237 (M+H+).

A mixture of 4 g (0.017 m) of the semicarbazone and 25 ml of ethanol was hydrogenated over 1 g of 10% palladium on charcoal until reaction was complete. The mixture was filtered. The combined filtrate-alcohol wash was concentrated. The residue was partitioned between water and ethyl acetate. The combined organic layer was washed with brine, dried and evaporated to give oily 4-methylindole which distilled at b.p. 62°–64° (0.05 mm), 1.77 g (80%), picrate, mp 194°–5° (f. methanol).

This reaction using the following starting materials gives the named intermediates and final products using standard isolation procedures:

(a) 2-nitrotoluene, 2-nitrophenylacetaldehyde semicarbazone, indole;

(b) 2-chloro-6-nitrotoluene, 6-chloro-2-nitrophenylacetaldehyde semicarbazone, 4-chloroindole;

(c) 4-bromo-6-nitrotoluene, 4-bromo-2-nitrophenylacetaldehyde semicarbazone, 6-bromoindole;

(d) 4,5-methylenedioxy-2-nitrotoluene, 4,5-methylenedioxy-2-nitrophenylacetaldehyde semicarbazone, 5,6-methylenedioxyindole;

(e) 4,5-dimethoxy-2-nitrotoluene, 4,5-dimethoxy-2-nitrophenylacetaldehyde semicarbazone, 5,6-dimethoxyindole;

(f) 4-fluoro-2-nitrotoluene, 4-fluoro-2-nitrophenylacetaldehyde semicarbazone, 6-fluoroindole;

(g) 2-nitro-p-cymene, 4-isopropyl-6-nitrophenylacetaldehyde semicarbazone, 6-isopropylindole.

EXAMPLE 3

A mixture of 18.12 g (0.1 m) of 2-methyl-3-nitrobenzoic acid, 53 ml (0.4 m) of dimethylformamide acetal and 40 ml of dimethylformamide was stirred and heated under a slow inlet of nitrogen (temp. 145°). After 18 hours, the mixture was worked up as above to give 2-carbomethoxy-6-nitro-$\beta$-dimethylaminostyrene.

This material (10 g) was converted to the semicarbazone and hydrogenated over palladium on charcoal as above to give 4-carbomethoxyindole, mp 66°–68° (lit. 79°). The carbethoxy indole is similarly prepared using dimethylformamide ethanal.

EXAMPLE 4

2,6-Dinitrotoluene (18.0 g, 0.1 m) is reacted with 0.15 mole of tris(dimethylamino)methane, then semicarbazide hydrochloride as in Example 1 to give 2,6-dinitrophenylacetaldehyde semicarbazone. This is hydrogenated as above in ethyl acetate to give 4-aminoindole, mp 106°–108°.

EXAMPLE 5

A mixture of 4.8 (0.1 m) of sodium hydride (50% dispersion washed out with hexane), 15.31 g (0.1 m) of nitrocresol and 50 ml of dimethylformamide was stirred for 5 minutes then 12.4 ml (0.104 m) of benzyl bromide was added followed by 21.75 g (0.15 m) of tris(dimethylamino)methane. The mixture was heated at reflux for 2 hours. After cooling, 22 g (0.2 m) of semicarbazide hydrochloride in 30 ml of water was added. The yellow precipitate was separated by filtration, adding water, washed with water and ethanol to give 28.37 g (86.5%) of yellow crystalline 2-benzyloxy-6-nitrophenylacetaldehyde semicarbazone, mp 188°–190° (d), mass spec. m/e 329 (M+H+).

A mixture of 6.56 g (0.02 m) of the semicarbazone, 28 ml of ammonium hydroxide and 12 ml of water was stirred as a mixture of 36 g (0.13 m) of ferrous sulfate and 40 ml of boiling water was added. After boiling for 30 minutes, the black precipitate was separated, washed with water and boiling ethyl acetate. The combined ethyl acetate extracts were dried and evaporated to give 4.67 of brown crystals. After sublimation and recrystallization from toluene/hexane, 3.17 g (71%) of 4-benzyloxy indole as white crystals, mp 70°–71°.

Catalytic hydrogenation as described above using palladium catalyst gave 4-hydroxyindole, 55% yield, mp 96°–98°.

What is claimed is:

1. A compound of the formula:

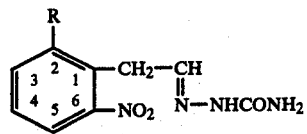

in which R is $C_{1-6}$ alkoxy, $C_{1-6}$-alkyl, benzyloxy or $C_{2-7}$-carbalkoxy.

2. The compound of claim 1 in which R is benzyloxy, being 2-benzyloxy-6-nitrophenylacetaldehyde semicarbazone.

3. The compound of claim 1 in which R is methoxy, being 2-methoxy-6-nitrophenylacetaldehyde semicarbazone.

4. The compound of claim 1 in which R is carbomethoxy, being 2-carbomethoxy-6-nitrophenylacetaldehyde semicarbazone.

* * * * *